US005607815A

United States Patent [19]
Bishop et al.

[11] Patent Number: 5,607,815
[45] Date of Patent: Mar. 4, 1997

[54] ULTRAHIGH CONTRAST BRIGHT LIGHT FILMS WITH RAPID PROCESSING

[75] Inventors: Julie C. Bishop, Old Bridge; John R. Shock, Princeton Junction, both of N.J.

[73] Assignee: E. I. Du Pont de Nemours and Company, Wilmington, Del.

[21] Appl. No.: 390,015

[22] Filed: Feb. 17, 1995

[51] Int. Cl.⁶ .................................................. G03C 1/09
[52] U.S. Cl. ...................... 430/264; 430/434; 430/435; 430/448; 430/605; 430/963
[58] Field of Search ........................... 430/264, 598, 430/963, 605, 434, 435, 448

[56] References Cited

U.S. PATENT DOCUMENTS

| | | | |
|---|---|---|---|
| 4,095,982 | 6/1978 | Yoneyama et al. | 430/434 |
| 4,681,836 | 7/1987 | Inoue et al. | 430/264 |
| 4,762,769 | 8/1988 | Takahashi et al. | 430/264 |
| 4,803,149 | 2/1989 | Takahashi et al. | 430/264 |
| 4,818,659 | 4/1989 | Takahashi et al. | 430/264 |
| 4,847,480 | 7/1989 | Miyata et al. | 430/264 |
| 4,851,321 | 7/1989 | Takagi et al. | 430/264 |
| 4,912,017 | 3/1990 | Takagi et al. | 430/264 |
| 4,937,160 | 6/1990 | Ruger | 430/264 |
| 4,939,067 | 7/1990 | Takagi et al. | 430/264 |
| 5,013,844 | 5/1991 | Ruger | 546/332 |
| 5,130,480 | 7/1992 | Ruger | 430/264 |
| 5,139,921 | 8/1992 | Takagi et al. | 430/264 |
| 5,190,847 | 3/1993 | Chan et al. | 430/264 |
| 5,252,449 | 10/1993 | Shock | 430/566 |
| 5,279,920 | 1/1994 | Onodera et al. | 430/264 |
| 5,340,704 | 8/1994 | Ezoe et al. | 430/434 |
| 5,384,232 | 1/1995 | Bishop et al. | 430/440 |

FOREIGN PATENT DOCUMENTS

| | | | |
|---|---|---|---|
| 0217260 | 4/1987 | European Pat. Off. | 430/264 |
| 2203256 | 10/1988 | United Kingdom | G03C 1/36 |
| 2206700 | 1/1989 | United Kingdom | G03C 1/36 |

Primary Examiner—Janet C. Baxter

[57] ABSTRACT

Disclosed are silver halide elements that contain an arylhydrazine compound useful in producing high contrast images. The elements can be handled in bright light room conditions for extended periods of time without increasing minimum density of the element.

19 Claims, No Drawings

ULTRAHIGH CONTRAST BRIGHT LIGHT FILMS WITH RAPID PROCESSING

BACKGROUND OF THE INVENTION

1. Field of the Invention

This invention relates to silver halide elements that contain an arylhydrazine compound useful in producing high contrast images. More particularly, this invention relates to ultrahigh contrast silver halide elements which can be handled in bright light room conditions and processed at a rapid rate.

2. Description of Related Art

Most conventional photographic materials are sensitive to visible light and, accordingly, must be handled under low intensity red, yellow, or amber lighting, commonly referred to as "darkroom conditions", to prevent undesired exposure of the material. Also known in the art, however, is a type of photographic material which can be handled under bright room conditions for a limited period of time without detrimental effects on the material. Such photographic materials are variously referred to in the art as "bright light films," "white light films," "daylight films," or "room light films".

Photographic materials which can be handled and processed in a bright room are specifically those which can be used in a room having illumination of at least 200 lux from a fluorescent lamp having reduced ultraviolet ray emission, or a filtered light not having the wavelength below about 420 nanometers (nm) as a safelight source. Typically, these photographic materials can be safely handled in bright room conditions on the order of 25 to 60 minutes, without detrimental effects on the film, such as fogging. To obtain such results, these photographic materials have greatly reduced sensitivity to visible light, that is about 1/1,000 to 1/10,000 that of ordinary darkroom photographic materials.

Exposing these photographic materials requires the use of a high intensity light source rich in ultraviolet light, such as, for example a high pressure mercury lamp, a metal halide lamp, a microwave discharge type mercury non-electrode light source, or a xenon lamp. To produce the high intensity required to expose bright light films, the above sources are broader than the point light sources used for conventional darkroom films and consequently emit more diffuse light. In order to obtain sharp character images, line images or dot images, by contact exposure of such bright light silver halide photographic material with a broad high intensity source, the photographic material is required to have a high contrast photographic characteristic, i.e., a contrast value of 10 or more. As is well known in the art, contact exposure is when a film is in contact with a negative during exposure. Various image forming systems for such materials have heretofore been provided.

To obtain the desired high contrast, the emulsion for the photographic material typically contains silver halide grains having a high proportion of silver chloride, which have been chemically sensitized by sulfur, noble metal, or reduction sensitizers or combinations thereof. Sulfur is the most common chemical sensitizer used. However, chemical sensitization, particularly sulfur sensitization, extends the intrinsic light absorption of the photographic emulsion to light wavelengths longer than 420 nm, reducing the room light tolerance of the photographic material.

To compensate for this effect, yellow dyes having a peak absorption in the range of 400 to 550 nm are typically added to the photographic emulsion layer and/or to a layer above the emulsion to reduce sensitivity to light above 420 nm wavelength. However, dyes added for the purpose of enhancing the safelight tolerance of these photographic materials often reduce the contrast enhancement arising from chemical sensitization.

Recently, the use of the lower wattage metal halide light sources and quartz iodide light sources has become increasingly popular because of decreased cost, energy savings and improved convenience of use. These lower wattage light sources, however, have reduced ultraviolet light emission, which means that the bright light films must have a higher sensitivity for use with these light sources. In order to provide typical desired contact exposure times of about 5 to 15 seconds, photographic materials designed for use with these lower wattage light sources require about an order of magnitude higher ultraviolet sensitivity compared to those designed for use with other high intensity light sources.

Furthermore, it is desirable to operate these lower energy light sources in a bright room, preferably in a room where the illumination intensity is fully equivalent to the typical office environment (about 540 lux). A method for preparing photographic silver halide emulsions having high tolerance to such room light conditions is described in U.S. Pat. No. 5,252,449. According to this method, rhodium-containing high chloride emulsions are sensitized by black and white developing agents. In the examples, mid-gradients, identified as contrast values, are limited to about 10.

There are applications, however, such as reverse imaging of very fine characters or the reproduction of images having soft edges, where ultrahigh contrast emulsions are needed to obtain high contrast images. "Ultrahigh contrast" in photographic silver halide elements is defined here as silver halide emulsions providing a contrast value above 15. Although litho development has been used to obtain ultrahigh contrast, development times are long, typically in excess of 1 minute, and the stability of the developer is limited to a few days. Aerial oxidation of the developer which gives rise to the stability problems is caused by the low sulfite content of these developers. Sulfite is generally added as a preservative to developers. Sulfite is low in litho developers because it interferes with the infectious litho development mechanism. To avoid these disadvantages, emulsions containing hydrazine derivatives have been used to produce ultrahigh contrast with developers high in sulfite content. The stability of the developer against aerial oxidation is greatly improved and development times are also reduced, generally to 30 to 45 seconds. However, to obtain rapid development, the pH of these developers has generally been high, often in excess of 11.6.

Methods for obtaining ultrahigh contrast in photographic elements at lower pH, e.g., pH of 10.8, by the use of particular aryl hydrazines described in U.S. Pat. Nos. 4,937,160, 4,939,067, 5,013,844, and 5,190,847, provide advantages in replenishment rates, disposal of exhausted solutions, and corrosion resistance of the development apparatus over the prior art. However, preferred emulsions for these inventions contain less than 50% chloride and the examples use emulsion containing either rhodium-free bromide or rhodium-free iodobromide grains, (2% mole iodide) developed in the range of 30 to 45 seconds. The application of photographic elements containing the aryl hydrazine is for the preparation of half tone images from continuous tone images, the reproduction of line images and photomasks for printed circuits or other products of photofabrication, and preparation of printing masters by phototypesetting.

The requirements for hydrazine technology are quite different, however, when used to produce ultrahigh contrast photographic silver halide elements designed for contact use under bright room conditions. As mentioned previously, the photographic elements used for these applications contain high chloride, preferably all chloride, grains which are desensitized with rhodium or iridium or other inorganic or organic agents. The desensitizing agents trap photoelectrons during exposure, reducing photographic sensitivity. However, they also can receive electrons donated by the hydrazine derivative during development, inhibiting nucleation of infectious development. While this effect can sometimes be overcome by adding relatively high levels of hydrazine derivative compounds, high levels of derivative compounds degrade safelight tolerance of these films, as well as coatability, sensitometric aging, and certain physical properties. Hence, very effective hydrazine derivatives are needed for room light contact films so that ultrahigh contrast can be obtained with acceptable amounts of the hydrazine compound. Also, it is imperative that any sulfur which may be part of the hydrazine derivative used in these emulsions be structurally bound in such a way that it does not become labile during the sensitization or development processes, resulting in the aforementioned reduction in safelight tolerance associated with sulfur sensitization.

Furthermore, the hydrazine derivatives for room light contact films need to be extremely effective nucleating agents to meet the rapid processing requirements for these systems, where the rapid access development time of at least 20 to 35 seconds is an industry expectation. The development time of hydrazine-containing systems can be accelerated by high pH development, i.e., pH of the developer around 11.6. But there are numerous aforementioned disadvantages of development at such high pH. U.S. Pat. No. 5,384,232 describes development accelerators, such as 1-phenethyl-2-picolinium bromide (PPB) and related derivatives which accelerate development of hydrazine-containing systems. However, the emulsions in the examples of pending application Ser. No. 08/040,247 contain 80% or less chloride and very little or no rhodium or other inorganic or organic desensitizers required for room light films.

SUMMARY OF THE INVENTION

In accordance with this invention there is provided a photosensitive element comprising:

a) a support; and b) at least one silver halide emulsion on the support, the emulsion comprising:

1) a Group VIII compound;

2) at least 85 mole % silver chloride grains; and 3) an arylhydrazine of the formula

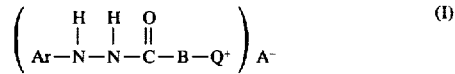

(I)

wherein

Ar is a substituted phenyl group with the proviso that the phenyl group is not substituted with thiourido or thiocarbomoyl;

B is a bridge that can contain one to three methylene groups, each of which can be substituted with methyl or ethyl, an oxygen atom, and —CO—NH— or —NH— groups;

$Q^+$ is an imidazolium, a substituted imidazolium, or an aminopyridinium group; and $A^-$ is an anion, and wherein the photosensitive element has a white light tolerance value of at least 15 minutes.

DESCRIPTION OF THE PREFERRED EMBODIMENT(S)

The present invention is a silver halide photosensitive element containing an arylhydrazine that can be handled in bright light conditions and rapidly developed for ultrahigh contrast and a process for making the element. Further, this invention is directed toward hydrazine derivatives whose nucleating effectiveness can be enhanced by development accelerators so that rapid development, preferably 20 second development, is achieved at relatively low pH, i.e., pH about 10.8 to 11.1, while not adversely affecting the roomlight tolerance of the film.

A silver halide emulsion of the present invention comprises silver halide grains comprising at least 85 mole % silver chloride. Preferred is 99.5 to 100 mole % silver chloride. More preferred is 100 mole % silver chloride grains for enhanced safelight tolerance under bright room conditions. The silver halide grains are not restricted in morphology and can be produced by any of the conventional methods, such as by splash, single jet, double-jet, or balanced double-jet or a combination thereof as is well known to those skilled in the art. The mean size of the silver halide grains of the present invention is generally less than 0.4 micron on an edge, assuming cubic morphology for grain volume determined by electronic reduction of the grain. Grains having 0.1 to 0.2 micron edge length, with cubic morphology, and narrow size distribution are preferred.

To desensitize the grains and further improve handling tolerance to bright room conditions, the emulsion contains a Group VIII metal salt preferably added during the silver halide grain formation process. Preferred are rhodium salt compounds which include, but are not limited to, rhodium dichloride, rhodium trichloride, potassium hexachlororhodate (III), ammonium hexachlororhodate (III), and sodium hexachlororhodate (III). The rhodium salt compounds can be added in an amount from $1\times10^{-7}$ to $1\times10^{-3}$ mole rhodium salt per mole silver in the emulsion.

These emulsions can then be dispersed in gelatin or other conventional silver halide binders and can also be further sensitized with chemical salts. Additionally, the emulsions prepared in this manner can also contain hardeners, antifoggants, wetting and coating adjuvants, matting agents, surfactants, and covering power adjuvants among others.

The term "high contrast" refers to the photographic imaging characteristic where the mid-gradient is at least 10 in order to get quality reproductions of original continuous tone images by means of a dot image or a reproduction of a line image. The term "ultrahigh contrast" refers to the photographic imaging characteristic where the mid-gradient is at least 15. It is preferred that photographic elements of this invention exhibit ultrahigh contrast, with mid-gradients greater than 15, most preferably greater than 20.

To define mid-gradient, a characteristic curve must be considered, which shows the relationship between density and exposure. Density is the measure of an image's ability to block the passage of light. Exposure is an indicator of the amount of radiant energy a photosensitive element may be subject to and exposure is the product of time and intensity of the radiation source. Because the characteristic curve is not a straight line, a single value cannot describe the entire curve. As such, the curve is broken down by density regions, to define which area of the curve is being measured. Mid-gradient relates to the rate of change of density with change in log exposure in the straight-line section (or middle portion) of a characteristic curve for a film. In this application, mid-gradient is the gradient between 0.35 and 1.50 density above base-plus-fog. Base-plus-fog (B+F) is the minimum density of a silver halide film resulting from the inherent density of the base layer of the film plus the fog density that is not due to exposure to light. The density points selected are dependent upon the product's characteristic curve when exposed to light, development conditions and the section of the curve most likely to be used in practice. A mid-gradient of 10 or 15 represents a high contrast film, which changes from clear areas (base) to black (high density areas) fairly quickly. Mid-gradient is the characteristic associated most with image sharpness to those of ordinary skill in the art. The higher the mid-gradient, the better the image sharpness.

The term "bright room conditions" as used herein, means an illumination of at least 200 lux with substantially no light with a wavelength less than 420 nm.

The term "white light tolerance value" (also referred to as safelight tolerance in this application) means the amount of time that a photosensitive element can be exposed to ultraviolet-filtered, i.e., wavelengths greater than about 420 nm, white room light of 540 lux before base-plus-fog density reaches 0.05. It is beneficial for the white light tolerance value to be at least 15 minutes for ultrahigh contrast photographic silver halide elements designed for contact use under bright room conditions, preferably 30 minutes and most preferably longer than 30 minutes.

Typical minimum base-plus-fog density of photographic elements on a non-tinted support is 0.02 to 0.03. Thus, the tolerance of a photographic element to white light can also be viewed as the amount of time that a photosensitive element can be exposed to ultraviolet-filtered white room light of 540 lux before base-plus-fog density increases by 0.02 density over the minimum base-plus-fog.

Surprisingly, we have found that the arylhydrazines represented by structure (I) can be added to photographic silver halide emulsions designed for roomlight use and obtain ultrahigh contrast while maintaining acceptable whitelight tolerance.

cycloalkyl with 5 to 7 carbon atoms; aralkyl or aralkoxy with one to three carbon atoms in the alkylene chain; an aliphatic acylamino radical with one to four carbon atoms which can be substituted with a sulfur atom which is further substituted with a substituent selected from the group consisting of alkyl with 1 to 5 carbon atoms, aryl, and aralkyl with 1 to 5 carbon atoms in the alkylene chain; an aliphatic acylamino radical with one to four carbon atoms which can be substituted with a heterocyclic ring of 5 to 7 carbon atoms containing —S—, the heterocyclic ring optionally substituted with methyl or ethyl; alkylthiophenylurido; and phenylurido. However, $R_2$ through $R_4$ cannot be thiourido or thiocarbomoyl and at least one of the radicals is not hydrogen.

In the instance of a substituent on the phenyl group containing a sulfur atom, the sulfur atom must be divalently linked to two carbon atoms. The use of arylhydrazine compounds in which the sulfur atom is not divalently linked to two carbon atoms, such as thiocarbomoyl and thiourido, results in high white light sensitivity, i.e., white light tolerance less than 15 minutes.

B is a bridge which connects the hydrazine part of the aryl hydrazine compounds of this invention to a quaternary nitrogen of $Q^+$. B can be one to three methylene groups, each of which can be substituted by methyl or ethyl; an oxygen atom, and —CO—NH— or —NH— groups. It is preferred that B is a methylene group.

$Q^+$ is a cation which connects to the bridge B at a nitrogen atom to form the quaternary nitrogen. $Q^+$ can be an imidazolium, a substituted imidazolium, or an aminopyridinium group. The substituted imidazolium can be substituted on the non-quaternary nitrogen with an alkyl or alkenyl group of 1 to 5 carbon atoms. The presence of an amino group on aminopyridinum provides the desired mid-gradient for ultrahigh contrast.

The anion $A^-$ is selected to balance the charge of the imidazolium, substituted imidazolium or amino pyridinium cation. The anion can be a halide anion, for example chloride, bromide or iodide ion.

Examples of the arylhydrazine compounds represented by structure (I) include, among others:

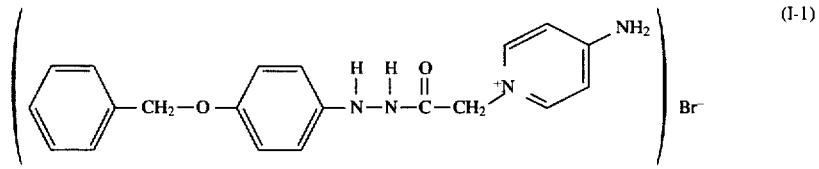

1-{(4-benzyloxyphenylhydrazido)methyl}-4-aminopyridinium bromide

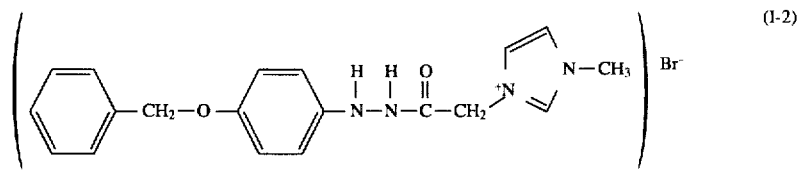

In structure (I), Ar is a substituted phenyl group of the structure

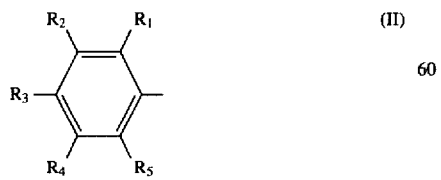

in which $R_1$ and $R_5$ are hydrogen and $R_2$ through $R_4$ are radicals which can be the same or different and which are represented by hydrogen; alkyl with 1 to 20 carbon atoms;

1-methyl-3-{(4-benzyloxyphenylhydrazido)methyl}imidazolium bromide

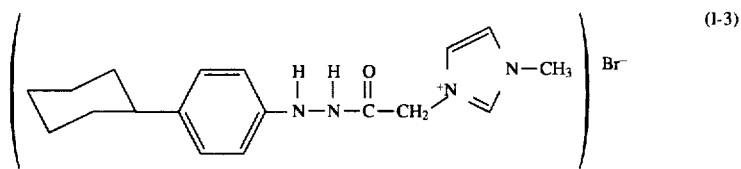

1-methyl-3-{(4-cyclohexylphenylhydrazido)methyl} imidazolium bromide

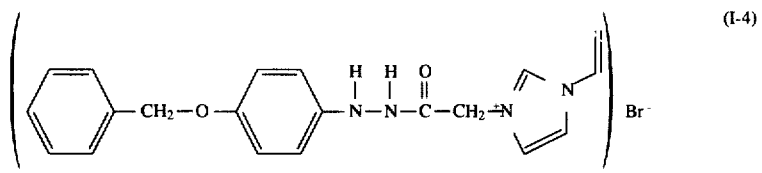

1-vinyl-3-{(4-benzyloxyphenylhydrazido)methyl} imidazolium bromide

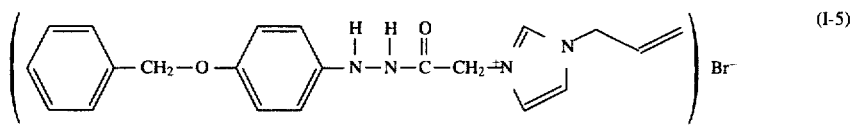

1-allyl-3-{(4-benzyloxyphenylhydrazido)methyl} imidazolium bromide

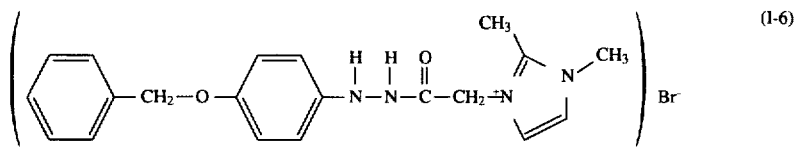

1,2-dimethyl-3-{(4-benzyloxyphenylhydrazido)methyl} imidazolium bromide

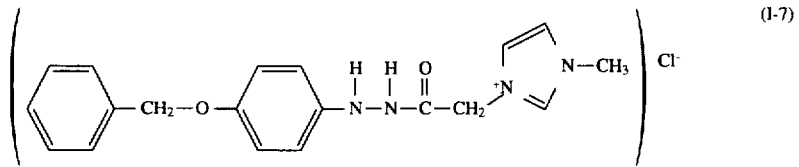

1-methyl-3-{(4-benzyloxyphenylhydrazido)methyl} imidazolium chloride

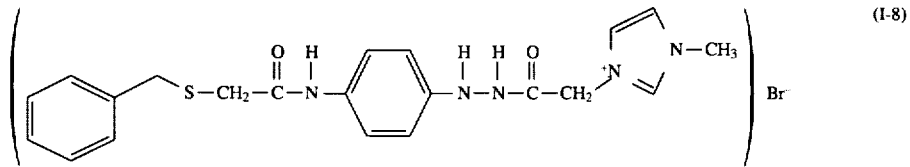

1-methyl-3-{(benzylthioacetamidophenylhydrazido)methyl}imidazolium bromide

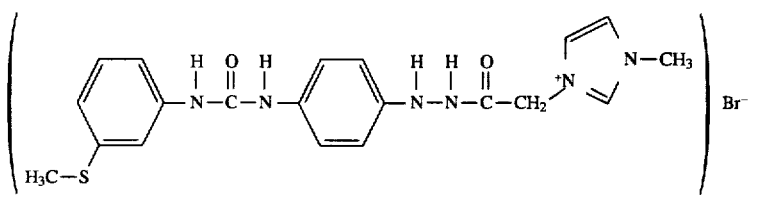

{1-methyl-3-(methylthiophenyluridophenylhydrazido)} methyl imidazolium, bromide

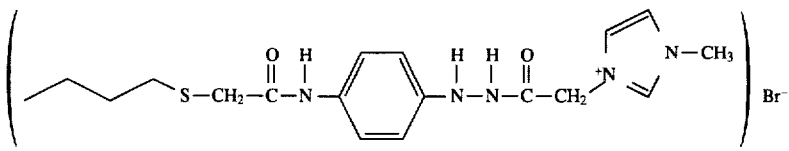

1-(butylthioactamidophenylhydrazidomethyl)-3-methyl imidazolium bromide

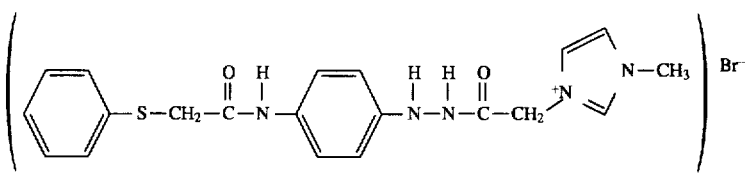

1(-phenylthioacetamidophenylhydrazidomethyl)-3-methyl imidazolium bromide

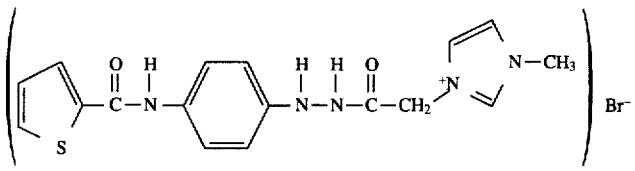

1-(2-thiphenecarboxyamidophenylhydrazidomethyl)-3-methyl imidazolium bromide

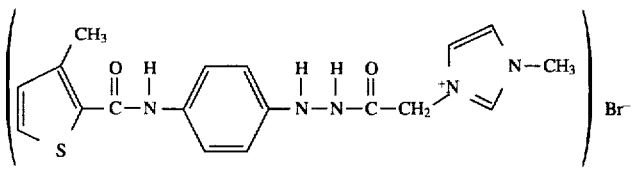

1-(3-methyl-2-thiphenecarboxyamidophenylhydrazidomethyl)-3-methyl imidazolium bromide

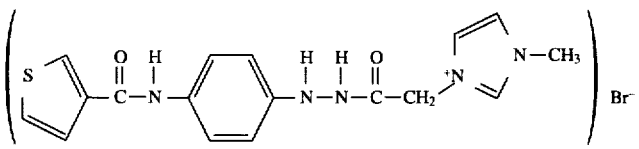

1-(3-thiphenecarbonyamidophenylhydrazidomethyl)-3-methyl imidazolium bromide

The synthesis of the arylhydrazine compounds is described in U.S. Pat. Nos. 4,937,160, 4,939,067, 5,013,844, and 5,190,847. These compounds can be made using reactions commonly known to any scientist skilled in the art.

The arylhydrazine compounds are generally added to the emulsions described above in amounts in excess of $1.0 \times 10^{-5}$ mole per mole of silver, and can be used as high as 1 mole per mole of silver or more. Preferred range of the compounds of structure (I) is between $1.0 \times 10^{-4}$ and $1.0 \times 10^{-2}$ mole per mole of silver. The arylhydrazine compounds may be added as a solid or dissolved in a suitable solvent that is compatible with the aqueous silver halide emulsion. Preferably, the arylhydrazines of this invention are dissolved in water or mixtures of water and alcohol when added to the silver halide emulsion. The solution used to dissolve the arylhydrazines of this invention must be compatible with the silver halide emulsion and yet must be able to suitably dissolve the hydrazine compound itself.

Preferred compounds are I-1, 1-2, I-4, I-5, I-6, I-7, I-8, I-9, 1-12, and 1-13. Particularly preferred hydrazines are those having a cationic imidazolium moiety. Particularly preferred is a chloride or bromide salt of 1-methyl-3-{(4-benzyloxyphenylhydrazido) methyl}imidazolium, Compound I-2.

While filter dyes are not required to obtain the desired bright room tolerance in the emulsions, they may be used to further improve that property, if desired. More preferably, filter dyes may be used in the emulsion to adjust the exposure latitude and speed of the photographic element. Exposure latitude refers to the range of exposures which provide faithful image reproduction during contact exposure. The filter dye may be incorporated in the silver halide emulsion or it may be present in another layer of the photographic element. Suitable dyes normally having the maximum absorption peak between 400 and 550 nm and tail or secondary absorption peak below 400 nm, such as for example, azo, oxonol, hemioxonol, cyanine, mericyanine dyes and the like, can be used.

To improve the dimensional stability of the photographic element, the emulsion may contain dispersions of synthetic polymer latices such as polymethyl acrylates, polyethylacrylates, and the like, used alone or in combination, as is well known in the art.

Development accelerators which are described in U.S. Pat. No. 5,384,232 may also be present in the system. Development accelerators may be used with this invention to increase contrast, commonly referred to as image sharpness, as well as to increase development rate. The contrast of a photographic element is reflected by the imaging characteristic, mid-gradient. The development accelerator can be added to the emulsion or to the developer. The development accelerator may be added as a solid or dissolved in water or some water-miscible solvent, such as acetone or one of the lower alcohols. If added to the developer, the development accelerators can be advantageously added in amounts from 0.05 gram to 1.5 gram/liter (g/l) of developer (working strength) and preferably in amounts from 0.25 g to 1.0 g per liter. Working strength refers to the aqueous form in which the developer is used as opposed to the concentrated form in which developers may be sold. Use of the term developer in this application should be construed to mean a developer at working strength. If added to the emulsion, the development accelerators are preferably employed in amounts of 0.05 g to 1.5 g per mole of silver. The development accelerators can also be included in a layer adjacent to the emulsion layer, such as an overcoat protective layer or an auxiliary layer. It is generally preferred to incorporate the development accelerators into the developer.

From U.S. Pat. No. 5,384,232, particularly preferred development accelerators are 1-phenethyl-2-picolinium chloride and 1-phenethyl-2-picolinium bromide. Other preferred development accelerators include ethyl-(a-pyridinium) acetate bromide, 1-phenethyl-4-(dimethylamino)pyridinium bromide, cetyl pyridinium bromide, 1-phenethyl-quinolinium bromide, 1-(N,N-dimethylacetamino) pyridinium chloride, 1-allyl-3-{(N,N-diethylammonium) ethyl} imidazolium chloride, 1-{(N,N-dimethylammonium) ethyl} dihydroquinoline bromide, 1-vinyl-3-{(N,N-diethylammonium) ethyl}imidazolium chloride, 1-phenethyl-4-methyl-pyridinium bromide, 1-allyl-3(2-dimethylaminoethyl) imidazolium chloride hydrochloride salt, 1-phenethyl-3,5-methyl-pyridinium bromide, 1-phenethyl-4-ethyl-pyridinium bromide, 1-ethylquinolinium iodide, 1-(3-sulfapropyl)pyridinium hydroxide inner salt, 1-ethyl-2-methylpyridinium bromide, 1,2 di-methylquinolinium methylsulfate, 1,4-(dipyridinium)butane dibromide, 1,3-(di-2-methylpyridinium)propane dibromide, 1-(2-phenethyl) isoquinolinium bromide, 1,6-(di-2-methylpyridinium)hexane dibromide, 1-4-di{(2-methylpyridinium)methyl}benzene dibromide, 1-(N,N-diethylaminoethyl)-pyridinium chloride hydrochloride salt, 1-((N,N-diethylamino)methyl)-4-(methyl)-pyridinium bromide, 1-methyl-3-((N,N-diethylaminoethylamido)methyl)-imidazolium bromide, 1-allyl-3-((N,N-diethylaminoethylamido)methyl)-imidazolium bromide, 1-((N,N-diethylaminoethylamido)methyl)-pyridinium bromide, 1-N,N-diethylaminoethyl pyridinium bromide hydrochloride salt, 1-N,N-diethylaminoethyl-4-(methyl)-pyridinium bromide hydrochloride salt, 1-(N,N-diethylaminoethyl)-imidazolium chloride hydrochloride salt, and poly(4-vinyl-1-(N,N-diethylaminoethyl)-pyridinium chloride hydrochloride salt).

After the emulsions are prepared and sensitized and the compounds of this invention added thereto, they can be coated on any conventional photographic support, such as the film supports known as polyesters. A preferred support is dimensionally stable polyethylene terephthalate. These supports may be suitably subbed with resin and/or gelatin layers as is conventional to make them receptive to the aqueous emulsion. The support may also have a backing layer coated on the side opposite to that containing the emulsion. These backing layers may be gelatino anticurl layers or may contain antihalation dyes, for example. Antistatic layers are now conventional and these too may be present. A thin, gelatin layer may be coated on top of the emulsion layer to serve as a protective layer.

After coating, these photosensitive elements are suitable for use as negative-working elements such as those commonly used in the printing and graphic arts industry which is preferred. The photosensitive elements can be handled in bright room conditions, including "white light" conditions with illumination intensities of about 540 lux, for extended periods of time, e.g., 15 to 60 plus minutes, without a substantial increase (about 0.02 to 0.03) in base-plus-fog (or minimum density) of the element. They can be given a conventional image-wise exposure with, for example, high intensity ultraviolet light or low intensity ultraviolet light, and then processed in any of the commonly available silver halide developing systems well-known in the art. These systems usually contain dihydroxybenzene compounds, e.g., hydroquinone, as the primary developing agent but also may contain small amounts of a super-additive developing agent such as the pyrazolidones. Developers containing ascorbic acid or derivatives thereof are also suitable to use. Development times are typically longer than one minute for litho developers and less than one minute, typically 30 to 45 seconds, in rapid processing developers. The development accelerator can be in the emulsion or developer. It is generally preferred to include a development accelerator in the developer. However, to obtain ultrahigh contrast with these photosensitive elements, it is generally preferred to have the developer pH balanced to at least 10.8, and, for rapid development times of 20 to 25 seconds, it is generally preferred to develop with a development accelerator present in the developer.

This invention will now be illustrated by, but not limited to, the following specific examples.

EXAMPLES

Examples 1 through 6

A cubic, monodisperse silver halide emulsion containing bromochloride grains having 0.5% mole bromide content, with an average grain size of 0.13 μm was prepared by balanced double jet procedures well known in the art. Sodium hexachlororhodate was added in an amount sufficient to insure that $8.44 \times 10^{-6}$ mole of rhodium per mole of silver halide was present. After the precipitation was accomplished, the soluble salts were removed by coagulation washing and the emulsion was reconstituted to a 9.6% silver analysis and 6% gelatin. A polyethyl acrylate latex in the amount of 46 g per mole silver was added as an agent to enhance film dimensional stability. A small amount of mercuric chloride, benzotriazole, and 4-hydroxy-6-methyl-1,3,3a,-7-tetraazaindene were added to the emulsion as stabilizers.

The emulsion was split into a number of portions and varying amounts of the aforementioned arylhydrazine compounds of the present invention were added to the various splits. These compounds were dissolved in water or mixtures of water and alcohol at the levels listed in Table 1. Each split or portion of emulsion was coated onto a 4 mil, dimensionally stable polyethylene terephthalate film support to a silver coating weight of about 3.9 g per square meter. Each emulsion coating was then overcoated with a thin layer of aqueous gelatin containing a formaldehyde hardener.

Similarly, other arylhydrazine compounds, not within the ambit of this invention, were added to splits for comparative purposes. The following other compounds were:

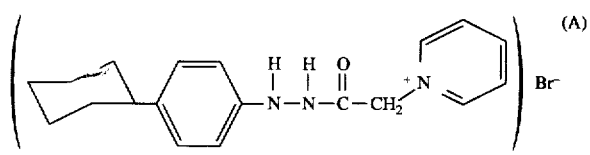

{(4-cyclohexylphenylhydrazido)methyl}pyridinium bromide

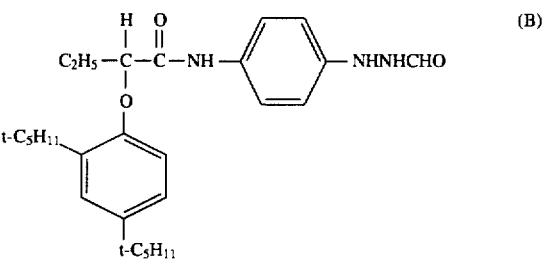
(B)

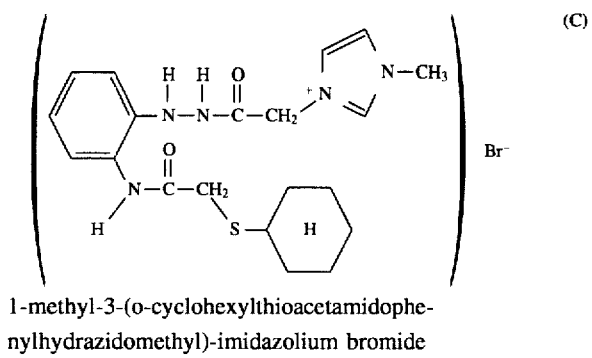
(C)

1-methyl-3-(o-cyclohexylthioacetamidophenylhydrazidomethyl)-imidazolium bromide

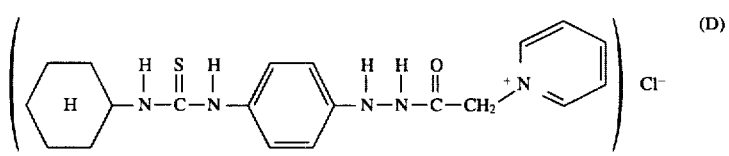
(D)

1-{(4-(cyclohexylthiourido)phenylhydrazido)methyl}pyridinium chloride

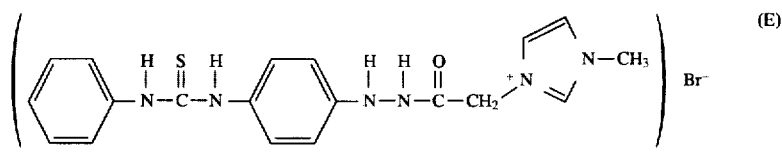
(E)

1-methyl-3-{(4-(phenylthiourido)phenylhydrazido)methyl} imidazolium bromide

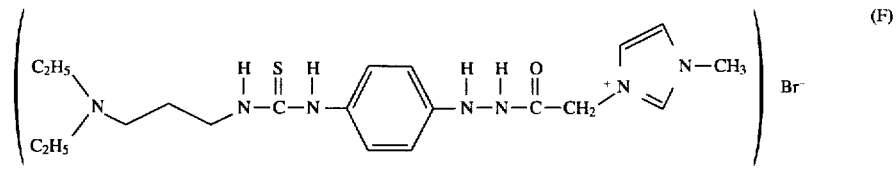
(F)

1-methyl-3-(p-diethylaminopropylthiouridophenyl-hydrazidomethyl) imidazolium bromide

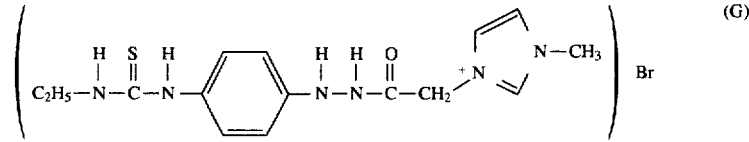
(G)

1-methyl-3-{(4-(ethylthiourido)phenylhydrazido)methyl} imidazolium bromide

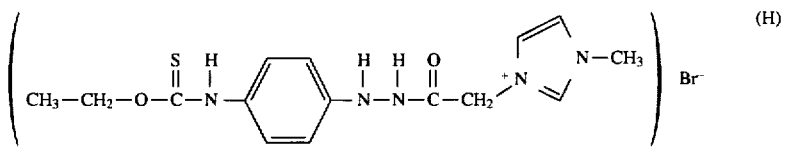

1-methyl-3-{(ethylthiocarbamoyl)phenylhydrazidomethyl} imidazolium bromide

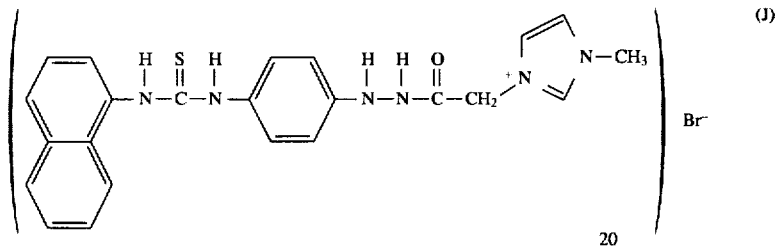

1-methyl-3-{4-(1-napthylthiourido)phenylhydrazido} methyl imidazolium bromide

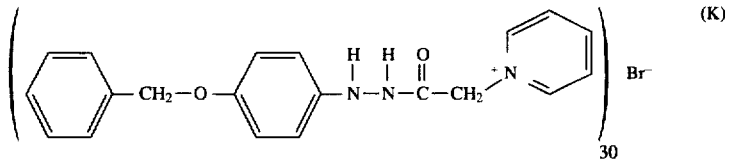

1-{(4-benzyloxyphenylhydrazido)methyl}pyridinium bromide

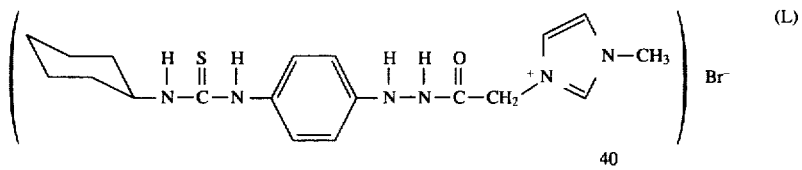

1-methyl-3-{(4-(cyclohexylthiourido)phenylhydrazido) methyl}imidazolium bromide.

After drying, sensitometric performance was evaluated for each coating. Each coating was exposed through a test image (3 log E continuous tone wedge) with a contact screen for 10 seconds to a quartz iodide lamp. The exposed samples were then developed for 35 seconds in the following developer at a pH of 10.9, followed by conventional fixing, washing and drying. Dot quality of the images was evaluated by visual inspection of dots with a 50X magnifier. The scale for dot quality was poor, good, and excellent in which good and excellent are acceptable for practical use, but excellent is preferred. Excellent dot quality indicates dots with hard, clean edges that have very little fringe around the edges.

| Developer composition: | |
|---|---|
| Ingredient | Amount/liter |
| Water | 525 ml[1] |
| Sequestrene Na₃ | 7.50 g |
| Sodium Bisulfite, 39% Liquid | 180 ml |
| Hydroquinone | 50.00 g |
| Elon (metol) | 5.00 g |
| Potassium Bromide | 8.00 g |
| Benzotriazole | 1.00 g |
| 1-Phenyl-5-Mercaptotetrazole | 0.12 g |

| -continued | |
|---|---|
| Developer composition: | |
| Ingredient | Amount/liter |
| Glucono-Delta-lactone | 2.00 g |
| 2-Mercaptobenzothiazole | 0.09 g |
| 1-Phenethyl-2-picolinium bromide (PPB) | 0.40 g |
| 2-Diethylaminoethanol | 30.00 g |
| Potassium Hydroxide, 45% liquid | 100 ml |
| Potassium carbonate, 47% liquid | 75 ml |
| pH was 10.8. | |

[1]ml = milliliters

Safelight tolerance was determined by exposing the coated film samples, emulsion side up, to 540 lux of illumination for the indicated times. The safelight time in minutes (min) represents the amount of time required before density increased by 0.02 over base-plus-fog density. Samples were illuminated with Sylvania Warm White 40 watt fluorescent bulbs covered with SuperWhite™ UV absorbing sleeves having an ultraviolet cut-off at 418 nm, model TD-901, made by Illumination Technology (Fairfield, NJ). The samples were then developed as described above and the density of the films was read using a McBeth densitometer.

TABLE 1

| Example | Comp ID | Amount Compound mole/1.5 mole AgX | Speed[1] | Grad[2] | Dot[3] Quality | B + F[4] Density after 15 min | B + F[4] Density after 20 min | B + F[4] Density after 30 min |
|---|---|---|---|---|---|---|---|---|
| Control | — | — | 229 | 6.2 | Poor | | 0.029 | 0.03 |
| Comp 1a | A | $3.9 \times 10^{-3}$ | 449 | 8.12 | Poor | | 0.033 | 0.038 |
| Comp 1b | A | $7.2 \times 10^{-3}$ | 522 | 5.42 | Poor | | 0.036 | 0.051 |
| Comp 2a | B | $5.8 \times 10^{-4}$ | 325 | 7.17 | Poor | | 0.031 | 0.032 |
| Comp 2b | B | $3.9 \times 10^{-3}$ | 288 | 6.1 | Poor | | 0.033 | 0.033 |
| Comp 2c | B | $7.2 \times 10^{-3}$ | 319 | 7.05 | Poor | | 0.032 | 0.033 |
| Comp 3a | C | $4.28 \times 10^{-4}$ | 471 | 9.53 | Poor | | 0.032 | 0.034 |
| Comp 3b | C | $8.56 \times 10^{-4}$ | 438 | 8.56 | Poor | | 0.031 | 0.033 |
| Comp 3c | C | $1.71 \times 10^{-3}$ | 457 | 9.43 | Poor | | 0.031 | 0.033 |
| Comp 4a | D | $4.28 \times 10^{-4}$ | 524 | 9.23 | Poor | 0.053 | 0.082 | 0.213 |
| Comp 4b | D | $8.55 \times 10^{-4}$ | 519 | 9.34 | Poor | 0.037 | 0.045 | 0.139 |
| Comp 4c | D | $1.28 \times 10^{-3}$ | 519 | 10.26 | Good | 0.037 | 0.044 | 0.119 |
| Comp 5a | E | $5.7 \times 10^{-4}$ | 517 | 9.23 | Poor | | 0.814 | 2.27 |
| Comp 5b | E | $8.53 \times 10^{-4}$ | 528 | 10.81 | Good | | 1.13 | 2.85 |
| Comp 5c | E | $11.4 \times 10^{-4}$ | 524 | 11.08 | Good | | 3.84 | 5.06 |
| Comp 6a | F | $2.85 \times 10^{-4}$ | 530 | 11.85 | Good | 0.046 | 0.071 | 0.131 |
| Comp 6b | F | $5.7 \times 10^{-4}$ | 551 | 12.53 | Good | 0.119 | 0.226 | 1.2 |
| Comp 6c | F | $11.4 \times 10^{-4}$ | 563 | 13.44 | Good | 0.428 | 0.876 | 3 |
| Comp 7a | G | $4.28 \times 10^{-4}$ | 537 | 10.31 | Good | | 0.16 | 0.56 |
| Comp 7b | G | $8.55 \times 10^{-4}$ | 541 | 10.54 | Good | | 0.63 | 2.15 |
| Comp 7c | G | $1.28 \times 10^{-3}$ | 527 | 10.84 | Good | | 0.46 | 1.42 |
| Comp 8a | H | $6.71 \times 10^{-4}$ | 601 | 17.69 | Good | | 6.13 | 7+ |
| Comp 9a | J | $1.07 \times 10^{-3}$ | 550 | 12.07 | Good | | >6.0 | >6.0 |
| Comp 10a | K | $5.8 \times 10^{-4}$ | 407 | 6.7 | Poor | | 0.029 | 0.029 |
| Comp 10b | K | $3.9 \times 10^{-3}$ | 605 | 13.83 | Good | | 0.029 | 0.029 |
| Comp 10c | K | $7.2 \times 10^{-3}$ | 640 | 13.45 | Good | | 0.029 | 0.029 |
| Comp 11a | L | $2.85 \times 10^{-4}$ | 522 | 10.51 | Good | | 0.034 | 0.05 |
| Comp 11b | L | $5.8 \times 10^{-4}$ | 525 | 12.68 | Good | | 0.032 | 0.05 |
| Comp 11c | L | $7.0 \times 10^{-4}$ | 526 | 11.9 | Good | | 0.033 | 0.042 |
| Comp 11d | L | $8.53 \times 10^{-4}$ | 527 | 12.09 | Good | | 0.037 | 0.062 |
| Comp 11e | L | $11.4 \times 10^{-4}$ | 563 | 13.44 | Good | | 0.034 | 0.05 |
| Exam 1a | I-1 | $3.9 \times 10^{-3}$ | 631 | 31.35 | Excel | | 0.031 | 0.054 |
| Exam 1b | I-1 | $7.2 \times 10^{-3}$ | 664 | 29.04 | Excel | | 0.034 | 0.072 |
| Exam 2a | I-2 | $5.8 \times 10^{-4}$ | 586 | 11.54 | Good | | 0.029 | 0.029 |
| Exam 2b | I-2 | $3.9 \times 10^{-3}$ | 617 | 25+ | Excel | | 0.029 | 0.03 |
| Exam 2c | I-2 | $7.2 \times 10^{-3}$ | 683 | 25+ | Excel | | 0.03 | 0.03 |
| Exam 3a | I-3 | $3.9 \times 10^{-3}$ | 461 | 19.17 | Excel | | 0.033 | 0.038 |
| Exam 3b | I-3 | $7.2 \times 10^{-3}$ | 506 | 22.89 | Excel | | 0.036 | 0.066 |
| Exam 4a | I-4 | $3.9 \times 10^{-3}$ | 621 | 25+ | Excel | | 0.031 | 0.049 |
| Exam 4b | I-4 | $7.24 \times 10^{-3}$ | 673 | 25+ | Excel | | 0.032 | 0.075 |
| Exam 5a | I-5 | $3.9 \times 10^{-3}$ | 642 | 25+ | Excel | | 0.031 | 0.046 |
| Exam 5b | I-5 | $7.24 \times 10^{-3}$ | 681 | 25+ | Excel | | 0.032 | 0.059 |
| Exam 6a | I-6 | $7.24 \times 10^{-3}$ | 679 | 25+ | Excel | | 0.032 | 0.065 |

[1] Speed is expressed arithmetically as the anti-logarithm of the relative log exposure at an optical density of 0.3 above base-plus-fog.
[2] The mid-gradient is measured between 0.35 to 1.50 densities above base-plus-fog.
[3] Excel = Excellent
[4] B + F is base-plus-fog density formed when each sample is developed after irradiation with a fluorescent lamp (GTE 40 W) made by Sylvania using a Super White UV absorbing sleeve with UV cutoff at 420 nm for 15, 20 and 30 minute exposures at 50 foot candles.

From Table 1 it can be seen from the comparison compounds that it is very difficult to increase the contrast while maintaining satisfactory safelight tolerance. For example, only Comp 8a of the comparison compounds exhibited acceptable contrast enhancement, i.e., mid-gradient greater than 15, but its safelight tolerance was extremely poor. Of the comparison compounds, like Comp 3a, that exhibited good safelight tolerance, the contrast enhancement was poor, as well as the dot quality. The compounds of this invention, however, gave excellent contrast enhancement without diminishing roomlight handling capability of the film under ultraviolet-filtered white light conditions.

Examples 7 through 17

An emulsion containing 100 mole % silver chloride grains made by the balanced double jet method as described in Examples 1–6, but having $3.68 \times 10^{-6}$ mole rhodium per mole of silver, was dispersed in a bulking amount of gelatin. The emulsion was split into portions and to each portion was added 4-hydroxy-6-methyl-1,3,3a,7-tetraazaindene, benzotriazole, and gold chloride before the same latex, surfactant and hardening agents as described in Examples 1–6 were added. Examples were made by adding to each split the arylhydrazine and amounts indicated in Table 2. The portions were coated at the same emulsion and overcoat coating weight as used for Examples 1–6 but oxonol yellow filter dye was added to the overcoat layer to adjust speed and improve safelight tolerance. The comparative examples were prepared in the same manner, only using the comparative arylhydrazine and amounts indicated in Table 2. A comparative compound not previously identified is

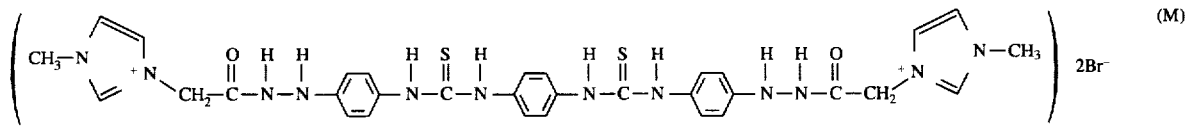

1,4 phenylene -di{(1-methyl-3-thiouridophenyl-hydrazido (methyl))imidazolium bromide}.

TABLE 2

| Compound I.D. | Amount Compound mole/1.5 mole AgX | Speed | Mid-Grad. | B + F Density After 30 min. | Safe Light Time (Min.) |
|---|---|---|---|---|---|
| Comp 12a | K | $2.4 \times 10^{-03}$ | 663 | 10.8 | 0.031 | 66 |
| Comp 12b | K | $7.4 \times 10^{-3}$ | 848 | 11.0 | 0.053 | 33 |
| Comp 13a | A | $2.4 \times 10^{-3}$ | 712 | 10.1 | 0.033 | 78 |
| Comp 13b | A | $7.4 \times 10^{-3}$ | 723 | 10.0 | 0.032 | 58 |
| Comp 14 | M | $2.4 \times 10^{-3}$ | 882 | 12.9 | >6.0 | 0 |
| Exam 7a | I-2 | $2.4 \times 10^{-3}$ | 728 | 32.3 | 0.036 | 72 |
| Exam 7b | I-2 | $7.3 \times 10^{-3}$ | 884 | 35.4 | 0.032 | 60 |
| Exam 8a | I-3 | $2.4 \times 10^{-3}$ | 675 | 9.9 | 0.034 | 75 |
| Exam 8b | I-3 | $7.3 \times 10^{-3}$ | 723 | 26.6 | 0.034 | 56 |
| Exam 9a | I-7 | $2.4 \times 10^{-3}$ | 735 | 22.0 | 0.035 | 54 |
| Exam 9b | I-7 | $7.3 \times 10^{-3}$ | 796 | 20.1 | 0.033 | 62 |
| Exam 10a | I-5 | $2.4 \times 10^{-3}$ | 852 | 35.7 | 0.033 | 48 |
| Exam 10b | I-5 | $4.8 \times 10^{-3}$ | 800 | 22.9 | 0.034 | 48 |
| Exam 11a | I-8 | $2.4 \times 10^{-3}$ | 798 | 24.5 | 0.034 | 52 |
| Exam 11b | I-8 | $4.8 \times 10^{-3}$ | 696 | 32.1 | 0.038 | 38 |
| Exam 12a | I-9 | $2.4 \times 10^{-3}$ | 844 | 49.9 | 0.033 | 39 |
| Exam 12b | I-9 | $4.8 \times 10^{-3}$ | 726 | 25.8 | 0.035 | 38 |
| Exam 13a | I-10 | $4.8 \times 10^{-3}$ | 867 | 29.6 | 0.054 | 19 |
| Exam 14a | I-11 | $2.4 \times 10^{-3}$ | 654 | 17.0 | 0.035 | 50 |
| Exam 14b | I-11 | $4.8 \times 10^{-3}$ | 767 | 30.7 | 0.036 | 48 |
| Exam 15a | I-12 | $2.4 \times 10^{-3}$ | 723 | 29.4 | 0.035 | 49 |
| Exam 15b | I-12 | $4.8 \times 10^{-3}$ | 777 | 36.8 | 0.035 | 45 |
| Exam 16a | I-13 | $2.4 \times 10^{-3}$ | 717 | 27.3 | 0.034 | 48 |
| Exam 16b | I-13 | $4.8 \times 10^{-3}$ | 759 | 35.8 | 0.035 | 50 |
| Exam 17 | I-14 | $4.8 \times 10^{-3}$ | 711 | 15.7 | 0.034 | 53 |

The films were evaluated in a developer which was the same as that used for Examples 1 through 6 except the amount of PPB was 0.5 g/liter of developer. The developer pH was 10.8. Also, a very rapid development time of 20 secs., preferred for contact film use, was used instead of 35 secs. The processed films were evaluated sensitometrically and for safelight tolerance in the manner described for Examples 1 through 6. The safelight time in minutes represents the amount of time required before density increased by 0.02 over base-plus-fog density. Safelight time in Table 2 is the time required to produce an 0.02 increase in optical density over base-plus-fog using the room light test conditions described for Examples 1 through 6.

The results in Table 2 clearly demonstrate that only the compounds of this invention give ultrahigh contrast, i.e., a mid-range gradient of greater than 15, which is needed for sharp images in critical applications, while maintaining the minimal acceptable white light room tolerance of 15 min.

Examples 18 through 22

Two photosensitive films made in the manner described for Examples 7 through 17, where the emulsion in one case contains the arylhydrazine I-2 and in the other case contains the comparative compound K, were developed for 20 secs. in the basic developer described in Examples 1 through 6, except that the developer accelerator compounds and amounts were varied according to Table 3. The mid-gradients for the processed films were determined by the method used for Examples 1 through 6. The development accelerator, 1-(N,N-diethylaminoethyl)-pyridinium chloride hydrochloride salt (DPC) has the following structure:

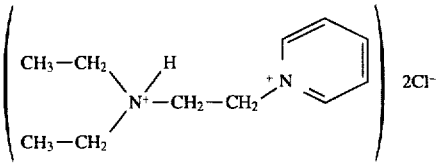

TABLE 3

| Example | Compound ID | Amount Compound Mole/1.5 Mole AgX | Development Accelerator PPB (g/l) | Development Accelerator DPC (g/l) | Mid-Grad. |
|---|---|---|---|---|---|
| Comp 15 | K | $7.3 \times 10^{-3}$ | 0.00 | 0.00 | 9.1 |
| Exam 18 | I-2 | $7.3 \times 10^{-3}$ | 0.00 | 0.00 | 10.4 |
| Comp 16 | K | $7.3 \times 10^{-3}$ | 0.50 | 0.00 | 8.3 |
| Exam 19 | I-2 | $7.3 \times 10^{-3}$ | 0.50 | 0.00 | 35.3 |
| Comp 17 | K | $7.3 \times 10^{-3}$ | 1.00 | 0.00 | 8.6 |
| Exam 20 | I-2 | $7.3 \times 10^{-3}$ | 1.00 | 0.00 | 44.3 |
| Comp 18 | K | $7.3 \times 10^{-3}$ | 0.00 | 0.39 | 9.0 |
| Exam 21 | I-2 | $7.3 \times 10^{-3}$ | 0.00 | 0.39 | 11.7 |
| Comp 19 | K | $7.3 \times 10^{-3}$ | 0.00 | 0.78 | 8.9 |
| Exam 22 | I-2 | $7.3 \times 10^{-3}$ | 0.00 | 0.78 | 15.8 |

The values reported in Table 3 indicate that the development rate of only the film containing an arylhydrazine of this invention is accelerated enough so that ultrahigh contrast is obtained at 20 sec. development. Also, higher contrast is obtained with the developer containing PPB at the 0.5 and 1.0 g/l developer levels than with DPC at equal molar levels, 0.39 and 0.78 g/l developer, respectively.

Examples 23 through 30

Photosensitive element films were made in the manner described for Examples 7 through 17, wherein the emulsion layer contains the arylhydrazine in the amount indicated in Table 4. The films were developed for 20 sec. in the same developer as that used for Examples 1 through 6, except for pH and PPB content, which were varied according to Table 4.

TABLE 4

| Example | Compound ID | Amount Compound Mole/1.5 Mole AgX | Developer pH | PPB (g/l) | Mid-Gradient |
|---|---|---|---|---|---|
| Exam 23 | I-1 | $7.3 \times 10^{-3}$ | 10.8 | 0.00 | 10.6 |
| Exam 24 | I-2 | $7.3 \times 10^{-3}$ | 11.1 | 0.00 | 11.2 |
| Exam 25 | I-2 | $7.3 \times 10^{-3}$ | 11.4 | 0.00 | 15.1 |
| Exam 26 | I-2 | $7.3 \times 10^{-3}$ | 11.7 | 0.00 | 24.3 |
| Exam 27 | I-2 | $7.3 \times 10^{-3}$ | 10.8 | 0.05 | 9.5 |
| Exam 28 | I-2 | $7.3 \times 10^{-3}$ | 10.8 | 0.50 | 29.8 |
| Exam 29 | I-2 | $7.3 \times 10^{-3}$ | 11.4 | 0.05 | 27.6 |
| Exam 30 | I-2 | $7.3 \times 10^{-3}$ | 11.4 | 0.50 | 53.2 |

Mid-gradients, which were determined by the process described for Examples 1 through 6, show that a developer containing PPB is as effective as having high pH for producing ultrahigh contrast at 20 sec. development time. In fact, with PPB at 0.5 g/liter developer level, higher contrast is obtained at pH 10.8 than is obtained with the PPB-free developer at 11.7 pH. Also, the effects on contrast of higher developer pH and PPB levels are additive as can be seen by the results of varying PPB level at pH 10.8 versus pH 11.4.

Examples 31 through 33

Photosensitive film elements were made in the manner described for Examples 7 through 17 wherein arylhydrazine, I-2, and the development accelerator, PPB, were incorporated into the emulsion layer in the amounts indicated in Table 5. The films were developed in developer which was the same as that used for Examples 1 through 6, except the pH was 10.8 and no PPB was present. Safelight time and the mid-gradient were determined in the manner described for Examples 1 through 6.

TABLE 5

| Example | I-2 Mole/1.5 Mole AgX | PPB Mole/1.5 Mole AgX | Mid-Gradient | B + F Density After 30 Min. | Safe-Light Time (Min.) |
|---|---|---|---|---|---|
| Exam 31 | $7.3 \times 10^{-3}$ | 0 | 10.4 | 0.036 | 56 |
| Exam 32 | $7.3 \times 10^{-3}$ | $8.8 \times 10^{-4}$ | 11.5 | 0.036 | 46 |

TABLE 5-continued

| Example | I-2 Mole/1.5 Mole AgX | PPB Mole/1.5 Mole AgX | Mid-Gradient | B + F Density After 30 Min. | Safe-Light Time (Min.) |
|---|---|---|---|---|---|
| Exam 33 | $7.3 \times 10^{-3}$ | $3.6 \times 10^{-3}$ | 17.2 | 0.042 | 36 |

The results in Table 5, which are for 20 sec. development, indicate that the contrast increases and safelight time, i.e., time to produce an 0.02 increase in B+F density, decreases as the level of PPB is increased in the emulsion layer.

Examples 34 through 36

The following examples demonstrate that the safelight tolerance of a film containing a compound of this invention is not impacted by the presence of a development accelerator in the developer.

A film was prepared as described above in Examples 1 through 6. Samples of the film were exposed and processed as described above except for the presence or absence of PPB, a development accelerator, in the developer and the development time as described in Table 6. Sensitometry and safelight tolerance were determined in the manner described in Examples 1 through 6.

TABLE 6

| Example | Cpd | Amount (mole/1.5 mole AgX) | Speed | Mid-Gradient | Development Accel. Present? | Dev. Time (sec) | Density after 20 min. to Safelight exposure |
|---|---|---|---|---|---|---|---|
| Exam 34 | I-4 | $3.9 \times 10^{-3}$ | 639 | 16.2 | no | 60 | 0.037 |
| Exam 35 | I-4 | " | 618 | 21.4 | yes | 25 | 0.037 |
| Exam 36 | I-4 | " | 617 | 31.5 | yes | 35 | 0.037 |

It is observed that although the safelight tolerance of the film is not impacted by the presence or absence of a development accelerator in the system, that the development accelerator provides a much higher contrast at shorter development times than the same developer without it.

Examples 37 through 39

An emulsion was prepared, coated, and tested as described in Examples 1 through 6 using I-2 as the arylhydrazine compound. The emulsion also contained as a development accelerator, poly(4-vinyl-1-(N,N-diethylamino ethyl)-pyridinium chloride hydrochloride salt), of the structure below in the amounts shown in Table 7. The polymeric development accelerator was dissolved in water and was added after the arylhydrazine compound.

TABLE 7

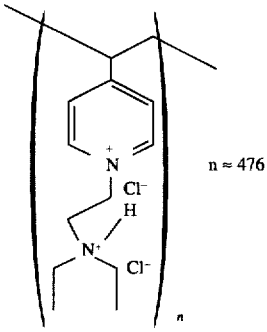

poly(4-vinyl-1-(N,N-diethylaminoethyl)pyridinium chloride hydrochloride salt)

n ≈ 476

| Example | Hydrazine I-2 (Mole/1.5 Mole AgX) | Polymeric Dev. Enhancer (g/1.5 mole AgX)* | Mid-Gradient | Speed | Dev. Time (sec.) | Safelight Time to reach 0.05 Dmin (Min) |
|---|---|---|---|---|---|---|
| 37 | $3.6 \times 10^{-3}$ | None | 19.4 | 567 | 30 | >60 |
| 38 | $3.6 \times 10^{-3}$ | 1.5 | 22.4 | 709 | 30 | 32 |
| 39 | $3.6 \times 10^{-3}$ | 3.0 | 26.3 | 769 | 30 | 32 |

*Amount reflects the total solid amount of the polymeric development accelerator contained in solution.

Speed and mid-gradient (contrast) increased as the amount of the polymeric development enhancer increased. Although the time to reach a Dmin. (base-plus-fog) of 0.05 for the films under safelight conditions described in Examples 1 through 6 was reduced from 60 minutes to 32 minutes by the presence of the development accelerator, the film still had white light tolerance acceptable within the scope of this invention.

What is claimed is:

1. A photosensitive element, comprising:
   a) a support; and
   b) at least one silver halide emulsion on the support, the emulsion comprising:
      1) a Group VIII compound;
      2) at least 85 mole % silver chloride grains; and
      3) an arylhydrazine of a formula

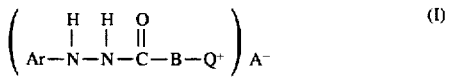  (I)

wherein

Ar is a substituted phenyl group with the proviso that the phenyl group is not substituted with thiourido or thiocarbomoyl;

B is a bridge containing one to three methylene groups, each of which is unsubstituted or substituted with a methyl group, and ethyl group, an oxygen atom, a —CO—NH— group or a —NH— group;

Q⁺ is an imidazolium, an imidazolium substituted on a non-quaternary nitrogen with an alkyl or alkenyl group of 1 to 5 carbon atoms; an imidazolium substituted on a non-quaternary nitrogen with an alkyl or alkenyl group of 1 to 5 carbon atoms and on a carbon atoms with a methyl group; or an aminopyridinium group; and A⁻ is an anion, and wherein the photosensitive element has a white light tolerance value of at least 15 minutes.

2. The photosensitive element of claim 1, wherein Ar is

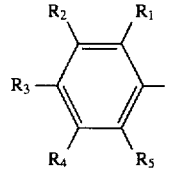

in which $R_1$ and $R_5$ are hydrogen and $R_2$ through $R_4$ are radicals which are the same or different and are hydrogen; alkyl with 1 to 20 carbon atoms; cycloalkyl with 5 to 7 carbon atoms; aralkyl or aralkoxy with one to three carbon atoms in an alkylene chain; an aliphatic acylamino radical with one to four carbon atoms which is unsubstituted or substituted with a sulfur atom and which is further substituted with a substituent selected from a group consisting of alkyl with 1 to 5 carbon atoms, aryl, and aralkyl with 1 to 5 carbon atoms in an alkylene chain; an aliphatic acylamino radical with one to four carbon atoms which is unsubstituted or substituted with a heterocyclic ring of 5 to 7 carbon atoms containing —S—, the heterocyclic ring unsubstituted or substituted with methyl, ethyl, alkylthiophenylurido, or phenylurido; and wherein at least one of the radicals is not hydrogen, and the radicals cannot be thiourido or thiocarbomoyl.

3. The photosensitive element of claim 1, wherein the arylhydrazine is selected from a group consisting of 1-{(4-benzyloxyphenylhydrazido)methyl}-4-aminopyridinium bromide, 1-methyl-3-{(4-benzyloxyphenylhydrazido)methyl}imidazolium bromide, 1-methyl-3-{(4-cyclohexylphenylhydrazido)methyl}imidazolium bromide, 1-vinyl-3-{(4-benzyloxyphenylhydrazido)methyl}imidazolium bromide, 1-allyl-3-{(4-benzyloxyphenylhydrazido)methyl}imidazolium bromide, 1,2-dimethyl-3-{(4-benzyloxyphenylhydrazido)methyl}imidazolium bromide, 1-methyl-3-{(4-benzyloxyphenylhydrazido)methyl}imidazolium chloride, 1-methyl-3-{(benzylthioacetamidophenyl-hydrazido)methyl}imidazolium bromide, {1-methyl-3-(methylthiophenyluridophenylhydrazido)}methyl imidazolium bromide, 1-(butylthioacetamidophenyl-hydrazidomethyl)-3-methyl imidazolium bromide, 1-(phenylthioacetamidophenyl-hydrazidomethyl)-3-methyl imidazolium bromide, 1-(2-thiophenecarboxyamidophenyl-hydrazidomethyl)-3-methyl imidazolium bromide, 1-(3-methyl-2-thiophenecarboxy-amindophenylhydrazidomethyl)-3-methyl imidazolium bromide, and 1-(3-thiphenencarbonyamidophenyl-hydrazidomethyl)-3-methyl imidazolium bromide.

4. The photosensitive element of claim 1, further comprising a mid-gradient of at least 15 after the element has been imagewise exposed.

5. The photosensitive element of claim 1, wherein the arylhydrazine is present in a range of $1.0 \times 10^{-5}$ to 1 mole per mole silver.

6. The photosensitive element of claim 1, wherein the Group VIII compound is a rhodium salt compound selected from a group consisting of rhodium dichloride, rhodium trichloride, potassium hexachlororhodate (III), ammonium hexachlororhodate (III), and sodium hexachlororhodate (III).

7. The photosensitive element of claim 6, wherein the rhodium salt compound is present in amounts from $1 \times 10^{-7}$ to $1 \times 10^{-3}$ mole rhodium salt per mole silver in the emulsion.

8. The photosensitive element of claim 1, wherein the emulsion comprises 100 mole % silver chloride grains.

9. The photosensitive element of claim 1, wherein the white light tolerance is greater than 20 minutes.

10. The photosensitive element of claim 1, wherein the white light tolerance is greater than 30 minutes.

11. The photosensitive element of claim 1, wherein the silver halide emulsion forms a layer on the support and the emulsion layer or a layer adjacent to the emulsion layer further comprises a development accelerator.

12. The photosensitive element of claim 11, wherein the development accelerator is present in amounts of 0.05 g to 1.5 g per mole of silver.

13. The photosensitive element of claim 11, wherein the development accelerator is selected from a group consisting of 1-phenethyl-2-picolinium chloride, 1-phenethyl-2-picolinium bromide, 1-phenethyl-4-(dimethylamino)pyridinium bromide, cetyl pyridinium bromide, 1-phenethyl-quinolinium bromide, 1-(N,N-dimethylacetamino) pyridinium chloride, 1-allyl-3-{(N,N-diethylammonium) ethyl} imidazolium chloride, 1-{(N,N-dimethylammonium)ethyl} dihydroquinoline bromide, 1-vinyl-3-{(N,N-diethylammonium) ethyl}imidazolium chloride, 1-phenethyl-4-methyl-pyridinium bromide, 1-allyl-3(2dimethylaminoethyl) imidazolium chloride hydrochloride salt, 1-phenethyl-3,5-methyl-pyridinium bromide, 1-phenethyl-4-ethyl-pyridinium bromide, 1-ethylquinolinium iodide, 1-(3-sulfapropyl)pyridinium hydroxide inner salt, 1-ethyl-2methylpyridinium bromide, 1,2 di-methylquinolinium methylsulfate, 1,4-(dipyridinium)butane dibromide, 1,3-(di-2-methylpyridinium)propane dibromide, 1-(2-phenethyl) isoquinolinium bromide, 1,6-(di-2-methylpyridinium)hexane dibromide, 1-4-di{(2-methylpyridinium)methyl}benzene dibromide, and 1-(N,N-diethylaminoethyl)-pyridinium chloride hydrochloride salt, 1-((N,N-diethylamino)methyl)-4-(methyl)pyridinium bromide, 1-methyl-3-((N,N-diethylaminoethylamido)methyl)-imidazolium bromide, 1-allyl-3-((N,N-diethylaminoethylamido)methyl)-imidazolium bromide, 1-((N,N-diethylaminoethylamido)methyl)-pyridinium bromide, 1-N,N-diethylaminoethyl pyridinium bromide hydrochloride salt, 1-N,N-diethylaminoethyl-4-(methyl)-pyridinium bromide hydrochloride salt, 1-(N,N-diethylaminoethyl)-imidazolium chloride hydrochloride salt, and poly(4-vinyl-1-(N,N-diethylaminoethyl)-pyridinium chloride hydrochloride salt).

14. A process for making a photographic element having an image of high contrast, comprising:
   a) providing a photosensitive element comprising
      i) a support; and
      ii) at least one silver halide emulsion on the support, the emulsion comprising:
         1) a Group VIII compound;
         2) at least 85 mole % silver chloride grains; and
         3) an arylhydrazine of a formula $$\left( \begin{array}{c} H \ H \ O \\ | \ | \ \| \\ Ar-N-N-C-B-Q^+ \end{array} \right) A^- \quad (I)$$

wherein

Ar is a substituted phenyl group with the proviso that the phenyl group is not substituted with thiourido or thiocarbomoyl;

B is a bridge containing one to three methylene groups, each of which is unsubstituted or substituted with a methyl group, and ethyl group, an oxygen atoms, a —CO—NH— group or a —NH— group;

$Q^+$ is an imidazolium, an imidazolium substituted on a non-quaternary nitrogen with an alkyl or an alkenyl group of 1 to 5 carbon atoms; an imidazolium substituted on a non-quaternary nitrogen with an alkyl or an alkenyl group of 1 to 5 carbon atoms and on a carbon atom with a methyl group; or an aminopyridinium group; and $A^-$ is an anion; and wherein the photosensitive element has a white light tolerance value of at least 15 minutes;

b) imagewise exposing the photosensitive element to ultraviolet light;

c) developing the exposed element in a developer at working strength.

15. The process of claim 14, wherein the developer contains a development accelerator.

16. The process of claim 15, comprising developing the exposed element in 25 seconds or less.

17. The process of claim 15, wherein the development accelerator is present in amounts of 0.05 g to 1.5 g per liter of developer.

18. The process of claim 15, wherein the development accelerator is selected from a group consisting of 1-phenethyl-2-picolinium chloride, 1-phenethyl-2-picolinium bromide, 1-phenethyl-4-(dimethylamino)pyridinium bromide, cetyl pyridinium bromide, 1-phenethyl-quinolinium bromide, 1-(N,N-dimethylacetamino) pyridinium chloride, 1-allyl-3-{(N,N-diethylammonium) ethyl} imidazolium chloride, 1-{(N,N-dimethylammonium) ethyl} dihydroquinoline bromide, 1-vinyl-3-{(N,N-diethylammonium) ethyl}imidazolium chloride, 1-phenethyl-4-methyl-pyridinium bromide, 1-allyl-3(2-dimethylaminoethyl) imidazolium chloride hydrochloride salt, 1-phenethyl-3,5-methyl-pyridinium bromide, 1-phenethyl-4-ethyl-pyridinium bromide, 1-ethylquinolinium iodide, 1-(3-sulfapropyl)pyridinium hydroxide inner salt, 1-ethyl-2-methylpyridinium bromide, 1,2 di-methylquinolinium methylsulfate, 1,4-(dipyridinium)butane dibromide, 1,3-(di-2-methylpyridinium)propane dibromide, 1-(2-phenethyl) isoquinolinium bromide, 1,6-(di-2-methylpyridinium)hexane dibromide, 1-4-di{(2-methylpyridinium)methyl}benzene dibromide, and 1-(N,N-diethylaminoethyl)-pyridinium chloride hydrochloride salt, 1-((N,N-diethylamino)methyl)-4-(methyl)pyridinium bromide, 1-methyl-3-((N,N-diethylaminoethylamido)methyl)-imidazolium bromide, 1-allyl-3-((N,N-diethylaminoethylamido)methyl)-imidazolium bromide, 1-((N,N-diethylaminoethylamido)methyl)-pyridinium bromide, 1-N,N-diethylaminoethyl pyridinium bromide hydrochloride salt, 1-N,N-diethylaminoethyl-4-(methyl)-pyridinium bromide hydrochloride salt, 1-(N,N-diethylaminoethyl)-imidazolium chloride hydrochloride salt, and poly(4-vinyl-1-(N,N-diethylaminoethyl)-pyridinium chloride hydrochloride salt).

19. The process of claim 14, wherein the pH of the developer is in the range of about 10.8 to about 11.1.

* * * * *